United States Patent [19]
Kokryakov et al.

[11] Patent Number: 5,633,229
[45] Date of Patent: May 27, 1997

[54] METHOD OF USING PROPHENINS-ANTIBIOTIC PEPTIDES

[75] Inventors: Vladimir N. Kokryakov, Los Angeles; Sylvia S. L. Harwig, Woodland Hills; Robert I. Lehrer, Santa Monica, all of Calif.

[73] Assignee: University of California, Los Angeles, Calif.

[21] Appl. No.: 487,359

[22] Filed: Jun. 7, 1995

Related U.S. Application Data

[63] Continuation of Ser. No. 222,798, Apr. 5, 1994.

[51] Int. Cl.$^6$ .......................... A61K 38/17; A61K 38/08
[52] U.S. Cl. .................................. 514/12; 514/15
[58] Field of Search .......................... 514/12, 15

[56] References Cited

U.S. PATENT DOCUMENTS

| | | | |
|---|---|---|---|
| 4,543,252 | 9/1985 | Lehrer et al. | 514/12 |
| 4,659,692 | 4/1987 | Lehrer et al. | 514/12 |
| 4,705,777 | 11/1987 | Lehrer et al. | 514/12 |

OTHER PUBLICATIONS

Broekaert et al., Antimicrobial Peptides from Amaranthus caudatus Seeds with Sequence Homology to the Cysteine/Glycine–Rich Domain o Chitin–Binding Proteins, Biochemistry (1992) 31:4308–4314.

Cornelissen et al., Strategies for Control of Fungal Disease with Transgenic Plants, Plant Physiol (1993) 101:709–712.

Delsal, G. et al., cDNA Cloning of the Neutrophil Bactericidal Peptide Indolicidin, Biochem Biophys Res Commun (1992) 187:467–472.

Diamond, G. et al., Tracheal antimicrobial peptide, a cysteine–rich peptide from mammalian tracheal mucosa: Peptide isolation and cloning of a cDNA; Proc Natl Acad Sci (USA) (1991) 88:3952–3958.

Diamond, G. et al., Airway epithelial cells are the site of expression of a mammalian antimicrobial peptide gene; Proc Natl Acad Sci USA (1993) 90:4596–4600.

Haln et al., Disease resistance results from foreign phytoalexin expression in a novel plant, Nature (1993) 361:153–156.

Harwig, S.S.L. et al., Primary Structure of Gallinacin–1, an Antimicrobial β–Defensin from Chicken Leukocytes, Techniques in Protein Chemistry V (1994) Academic Press Inc., New York, pp. 81–88.

Kokryakov et al., Protegrins: leukocyte antimicrobial peptides that combine features of corticostatic defensins and tachyplesins; FEBS (1993) 337:231–236.

Lambert et al., Insect Immunity: Isolation from immune blood of the dipteran Phormia terranovae of two insect antibacterial peptides with sequence homology to rabbit lung macrophage bactericidal peptides, Proc. natl. Acad. Sci. (USA) (1989) 88:262–265.

Larrick, J.W. et al., Complementary DNA Sequence of Rabbit CAP18–A Unique Lipopolysaccharide Binding Protein; Biochem Biophys Res Commun (1991) 179:170–175.

Lehrer et al., Direct Inactivation of Viruses by MCP–1 an MCP–2 Natural Peptide Antibiotics from Rabbit Leukocytes; J. Virol. (1985) 54:467–472.

Lehrer, R.I. et al., Defensins: Endogenous Antibiotic Peptides of Animal Cells, Cell (1991) 64:229–230.

Lehrer, R.I. et al., Defensins: Antimicrobial and Cytotoxic Peptides of Mammalian Cells, Ann Rev Immunol (1993) 11:105–128.

(List continued on next page.)

*Primary Examiner*—Robert A. Wax
*Assistant Examiner*—Kawai Lau
*Attorney, Agent, or Firm*—Morrison & Foerster LLP

[57] ABSTRACT

Peptide-based compounds containing multiple proline residues are useful as preservatives and in preventing, treating, or ameliorating microbial infection, especially Gram-negative bacterial infection in animals and plants, in treating conditions characterized by the presence of LPS. These compounds are of the formula

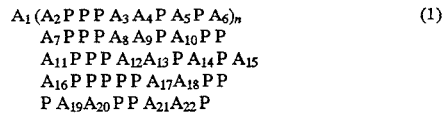

including the N-terminal acylated and/or C-terminal amidated or esterified forms thereof wherein each of $A_1$, $A_5$, $A_{10}$, $A_{14}$ and $A_{20}$ is independently Ala, Gly or Ser;

each of $A_2$, $A_4$, $A_7$, $A_9$, $A_{11}$, $A_{12}$, $A_{13}$, $A_{16}$, $A_{17}$, $A_{19}$ and $A_{22}$ is independently a hydrophobic amino acid selected from the group consisting of Ile, Leu, Val, Phe and Met;

each of $A_3$ and $A_8$ is independently a neutral polar amino acid selected from Asn and Gln or is a hydrophobic amino acid selected from the group consisting of Ile, Leu, Val, Phe and Met;

each of $A_6$, $A_{18}$ and $A_{21}$ is independently a basic amino acid selected from Arg, Lys, and Har; and wherein $A_{15}$ is Trp or a basic amino acid selected from Lys, Arg and Har;

wherein n is an integer of 1–6; and the antimicrobial or LPS-binding fragments thereof. Recombinant materials for the production of these peptides are also disclosed.

5 Claims, 4 Drawing Sheets

OTHER PUBLICATIONS

Levy, O. et al., Antibacterial 15-kDa Protein Isoforms (p15s) are Members of a Novel Family of Leukocyte Proteins, J. Biol Chem (1993) 268:6058–6063.

Miyata, T. et al., Antimicrobial Peptides, Isolated from Horseshoe Crab Hemocytes, Tachyplesin II, and Polyphemiusins I and II: Chemical Structures and Biological Activity, J Biochem (1989) 106:663–668.

Mirgorodskaya, O.A. et al., Primary Structure of Three Cationic Peptides from Porcine Neutrophils, FEBS (1993) 330:339–342.

Murakami, T. et al., Direct Virus Inactivation of Tachyplesin I and Its Isopeptides from Horseshoe Crab Hemocytes, Chemotherapy (1991) 37:327–334.

Morimoto, M. et al., Inhibitory Effect of Tachyplesin I on the Proliferation of Human Immunodeficiency Virus in vitro, Chemotherapy (1991) 37:206–211.

Nakamura, T. et al., Tachyplesin, A Class of Antimicrobial Peptide from the Hemocytes of the Horseshore Crab (Tachypleus tridentatus), J Biol Chem (1988) 263:16709–16713.

Nakashima, H. et al., Anti-Human Immunodeficiency Virus Activity of a Novel Synthetic Peptide, T22 ([Tyr-5,12, Lys-7]Polyphemiusin II): a Possible Inhibitor of Virus-Cell Fusion, Antimicrobial Agents and Chemotherapy (1992) 1249–1255.

Pungercar, J. et al., Molecular Cloning of a Putative Homolog of Proline/arginine-rich Antibacterial Peptides from Porcine Bone Marrow, FEBS (1993) 336:284–288.

Selsted, M.E. et al., Purification, Primary Structures, and Antibacterial Activities of β-Defensins, a New Family of Antimicrobial Peptides from Bovine Neutrophils, J. Biol Chem (1993) 288:6641–6648.

Storici, P. et al., A Novel cDNA Sequence Encoding a Pig Leukocyte Antimicrobial Peptide with a Cathelin-like Pro-sequence, Biochem Biophys Res Commun (1993) 196:1363–1368.

Storici, P., et al., cDNA Sequence Analysis of an Antibiotic Dodecapeptide from Neutrophils, FEBS (1992) 314:187–190.

Storici, P. et al., A cDNA Derived from Pig Bone Marrow Cells Predicts a Sequence Identical to the Intestinal Antibacterial Peptide PR-30[1], Biochem Biophys Res Commun (1993) 196:1058–1065.

Tang, Y–Q., et al. Characterization of the Disulfide Motif in BNBD-12, an Antimicrobial β-Defensin Peptide from Bovine Neutrophils, J Biol Chem (1993) 268:6649–6653.

Williamson, M.P. et al., The Structure and Function of Proline-rich Regions in Proteins, Biochem J (1994) 297:249–260.

Zanetti, M. et al., The cDNA of the Neutrophil Antibiotic Bac5 Predicts a Pro-sequence Homologous to a Cysteine Proteinase Inhibitor that is Common to Other Neutrophil Antibiotics, J Biol Chem (1993) 268:522–526.

```
A    F  P  P  P  N  V  P  G  P  R
     F  P  P  P  N  F  P  G  P  R
     F  P  P  P  N  F  P  G  P  R
     F  P  P  P  N  F  P  G  P  R
     F  P  P  P  N  F  P  G  P  P
     F  P  P  P  I  F  P  G  P  W
     F  P  P  P  P  P  F  R  P  P
        P  F  G  P  P  R  F  P
```

METHOD OF USING PROPHENINS-ANTIBIOTIC PEPTIDES

This invention was made with funding from NIH Grant No. AI22839. The U.S. Government has certain rights in this invention.

This application is a continuation of application Ser. No. 08/22,798 filed 5, Apr. 1994.

TECHNICAL FIELD

The invention relates to the field of antibiotic peptides. In particular, the invention concerns peptides, some of which can be isolated from porcine leukocytes, that are particularly effective against Gram-negative bacteria and can mitigate the symptoms of septic shock.

BACKGROUND ART

One of the defense mechanisms against infection by both animals and plants is the production of peptides that have antimicrobial and antiviral activity. Various classes of these peptides have been isolated from tissues both of plants and animals. One well known class of such peptides is the tachyplesins which were first isolated from the hemocytes of the horseshoe crab as described by Nakamura, T. et al. *J Biol Chem* (1988) 263:16709–16713. This article described the initial tachyplesin isolated from the Japanese species, Tachyplesin I, which is a 17-amino acid amidated peptide containing four cysteine residues providing two intramolecular cystine bonds. In a later article by this group, Miyata, T. et al. *J. Biochem* (1989) 206:663–668, extends the studies to the American horseshoe crab and isolated a second tachyplesin, Tachyplesin II, consisting of 17 residues amidated at the C-terminus, also containing four cysteine residues and two intramolecular disulfide bonds. Two additional 18-mers, called polyphemusins, highly homologous to Tachyplesin II and containing the same positions for the four cysteine residues, were also isolated. Polyphemusin I and Polyphemusin II differ from each other only in the replacement of one arginine residue by a lysine. All of the peptides were described as having antifungal and antibacterial activity. A later article by Murakami, T. et al. *Chemotherapy* (1991) 37:327–334, describes the antiviral activity of the tachyplesins with respect to vesicular stomatus virus; Herpes Simplex Virus I & II, Adenovirus I, Reovirus II and Poliovirus I were resistant to inactivation by Tachyplesin I. Morimoto, M. et al. *Chemotherapy* (1991) 37:206–211, found that Tachyplesin I was inhibitory to Human Immunodeficiency Virus. This anti-HIV activity was found also to be possessed by a synthetic analog of Polyphemusin II as described by Nakashima, H. et al. *Antimicrobial Agents and Chemotherapy* (1992) 1249–1255. Antiviral peptides have also been found in rabbit leukocytes as reported by Lehrer, R. I. et al. *J. Virol* (1985) 54:467–472.

Another class of antimicrobial and antiviral peptides, the "protegrins" have been isolated from porcine leukocytes as reported by the present applicants in a paper by Kokryakov, V. N. et al. *FEBS* (1993) 337:231–236. An additional paper disclosing cationic peptides from porcine leukocytes was published by Mirgorodskaya, O. A. et al. *FEBS* (1993) 330:339–342. Storici, P. et al. *Biochem Biophys Res Comm* (1993) 196:1363–1367, report the recovery of a DNA sequence which encodes a pig leukocyte antimicrobial peptide with a cathelin-like prosequence and is reported to be one of the protegrins.

Other important classes of cysteine-containing antimicrobial peptides include the defensins, β-defensins and insect defensins. The defensins are somewhat longer peptides characterized by six invariant cysteines and three intramolecular cystine disulfide bonds. Defensins were described by Lehrer, R. I. et al. *Cell* (1991) 64:229–230; Lehrer, R. I. et al. *Ann Rev Immunol.* (1993) 11:105–128. A review of mammalian-derived defensins by Lehrer, R. I. et al. is found in *Annual Review Immunol* (1993) 11:105–128; three patents have issued on the defensins: U.S. Pat. No. 4,705,777; U.S. Pat. No. 4,659,692; and U.S. Pat. No. 4,543,252. Defensins have been found in the polymorphonucleated leukocytes (PMN) of humans and of several other animals, as well as in rabbit pulmonary alveolar macrophages, and in murine small intestinal epithelial (Paneth) cells and in corresponding cells in humans.

β-Defensins are found in bovine leukocytes and respiratory epithelial cells. See Selsted, M. E. et al. *J. Biol Chem* (1993) 288:6641–6648, Tang, Y-Q. *J Biol Chem* (1993) 268:6649–6653, and Diamond, G. et al. *Proc. Natl Acad Sci (USA)* (1991) 88:3952–3958. Diamond, G. et al. *Proc Natl Acad Sci USA* (1993) 90:4596–4600. Insect defensins have been reported by Lambert, J. et al. *Proc Natl Acad Sci (USA)* (1989) 88:262–265.

Antifungal and antibacterial peptides and proteins have also been found in plants (Broekaert, W. F. et al. *Biochemistry* (1992) 31:4308–4314) as reviewed by Cornelissen, B. J. C. et al. *Plant Physiol* (1993) 101:709–712. Expression systems for the production of such peptides have been used to transform plants to protect the plants against such infection as described, for example, by Haln, R. et al. *Nature* (1993) 361:153–156.

Another group of antibacterial peptides which are isolated from avian leukocytes are the gallinacins. These peptides have cysteine distribution patters which are similar to the β-defensins obtained from mammalian species. These peptides are described by Harwig, S. S. L. et al. in *Techniques in Protein Chemistry V* (1994) Academic Press Inc., New York, pages 81–88.

An interesting feature of many of the apparently unrelated naturally occurring antimicrobial peptides is that they are derived from precursors which have similar 5' regions highly homologous to a porcine cysteine proteinase inhibitor, cathelin. For example, Storici, P. et al. *Biochem Biophys Res Commun* (1993) 196:1363–1368, point out that the β-defensins, as well as certain other classes of antimicrobial peptides share this common upstream region. These peptides include Bac5 (Gennaro, et al. *Infect Immun* (1989) 57:3142–3146 for which the cDNA was reported by Zanetti, M. et al. *J Biol Chem* (1993) 268:522–526); indolicidin (Selsted, M. E. et al. *J Biol Chem* (1992) 267:4292–4295; Delsal, G. et al. *Biochem Biophys Res Commun* (1992) 187:467–472); an acyclic dodecapeptide from bovine sources (Romeo, D. et al. *J Biol Chem* (1988) 263:9573–9575) for which a cDNA clone was reported by Storici, P., et al. *FEBS* (1992) 314:187–190); and CAP18 from rabbit leukocytes (Larrick, J. W. et al. *Biochem Biophys Res Commun* (1991) 179:170–175). This upstream sequence is also shared by the antibacterial 15 kD proteins, "p15", from rabbit polymorphonuclear leukocytes described by Levy, O. et al. *J. Biol Chem* (1993) 268:6058–6063. Still another member of this family is the PR39 peptide described by Storici, P. et al. *Biochem Biophys Res Commun* (1993) 196:1058–1065. All of these are characterized by prosequences homologous to the cysteine proteinase inhibitor, cathelin/PLCPI.

Taking advantage of this precursor homology, Pungercar, J. et al. *FABS* (1993) 336:284–288 (the December issue)

utilized a PCR-derived probe obtained by amplification of the propeptide region of a rabbit Cap18 cDNA to screen a cDNA library prepared in λ-GT11 from pig bone marrow. The retrieved cDNA clone contained a deduced amino acid sequence with the cathelin N-terminal sequence and a putative 100-amino acid residue mature protein rich in proline. These authors further suggest that the C-terminal 3-amino acid residue may be cleaved in the mature form to yield a 97-amino acid mature protein with multiple proline residues.

The effect of proline-rich regions on the structure and function of various proteins has been reviewed by Williamson, M. P. et al. *Biochem J* (1994) 297:249–260. Most of such proteins serve a structural or binding purpose since the presence of multiple proline residues imposes severe conformational constraints.

The present invention is directed to a family of proline-rich antimicrobial peptides containing about 79 amino acid residues with repeating decamer regions. The invention peptides are particularly effective against Gram-negative bacteria and also are capable of binding lipopolysaccharide (LPS) thus having the ability to mitigate the symptoms of septic shock. They are useful as preservatives and therapeutics. This class of peptides is designated "prophenins".

DISCLOSURE OF THE INVENTION

The invention is directed to prophenins, i.e., peptides of about 79 amino acid residues characterized by repeating decamer regions and a multiplicity of proline residues, as well as to fragments thereof with antimicrobial and/or LPS binding activity. These peptides can be produced synthetically and some can be produced recombinantly or can be isolated from their native sources and purified for use as preservatives or in pharmaceutical compositions in treating or preventing infection or septic shock in animals. Alternatively, the peptides can be formulated into compositions which can be applied to plants to protect them against microbial infection. In still another approach, the DNA encoding the peptides can be expressed in situ, in animals or preferably in plants, to combat infections. The peptides are also useful as standards in antimicrobial assays and in endotoxin or endotoxin inhibition assays and in binding endotoxins.

Accordingly, in one aspect, the invention is directed to a peptide in isolated and purified form of the formula:

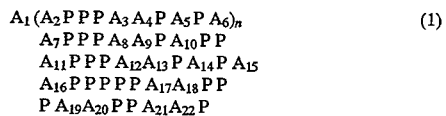

including the N-terminal acylated and/or C-terminal amidated or esterified forms thereof wherein each of $A_1$, $A_5$, $A_{10}$, $A_{14}$ and $A_{20}$ is independently Ala, Gly or Ser;

each of $A_2$, $A_4$, $A_7$, $A_9$, $A_{11}$, $A_{12}$, $A_{13}$, $A_{16}$, $A_{17}$, $A_{19}$ and $A_{22}$ is independently a hydrophobic amino acid selected from the group consisting of Ile, Leu, Val, Phe and Met;

each of $A_3$ and $A_8$ is independently a neutral polar amino acid selected from Asn and Gln or is a hydrophobic amino acid selected from the group consisting of Ile, Leu, Val, Phe and Met;

each of $A_6$, $A_{18}$ and $A_{21}$ is independently a basic amino acid selected from Arg, Lys, and Har; and wherein $A_{15}$ is Trp or a basic amino acid selected from Lys, Arg and Har;

wherein n is an integer of 1–6; and the antimicrobial or LPS-binding fragments thereof.

Some of the peptides of the invention are isolatable from porcine or other mammalian leukocytes by the methods similar to those described herein.

In still other aspects, the invention is directed to recombinant materials useful for the production of the peptides of the invention as well as to cells, plants or nonhuman animals modified to contain expression systems for the production of these peptides. The invention is also directed to pharmaceutical compositions and to compositions for application to plants containing the peptides of the invention as active ingredients or compositions which contain expression systems for production of the peptides for in situ expression of the nucleotide sequence encoding these peptides. The invention is also directed to methods to prepare the invention peptides synthetically, to antibodies specific for these peptides, and to the use of the peptides as preservatives. The invention is also directed to methods to mitigate the symptoms of toxic shock by administering the peptides of the invention.

In other aspects, the invention is directed to the use of the compounds of the invention as standards in antimicrobial and endotoxin binding or inhibition assays. The invention is also directed to use of the invention compounds as preservatives for foods or other perishables.

MODES OF CARRYING OUT THE INVENTION

Figure 1:
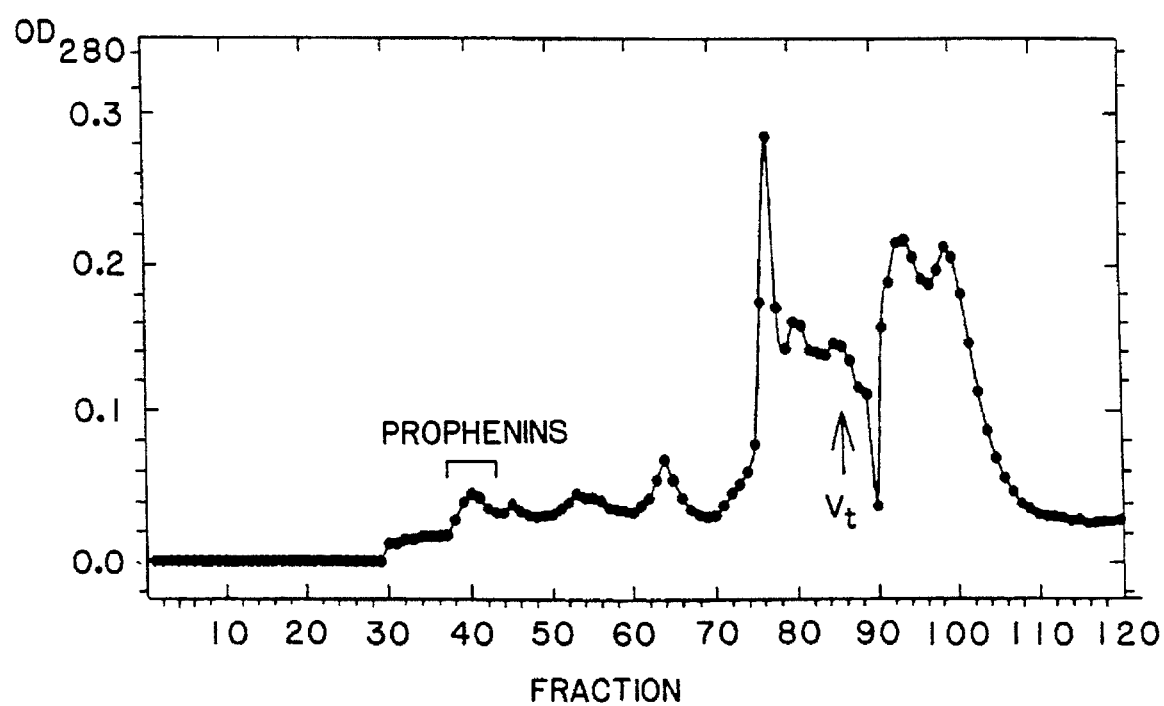
FIG. 1 shows the elution pattern of a concentrate of the ultrafiltrate of porcine leukocytes applied to an Biogel P10 column; $V_t$ signifies total column, volume.

The prophenin peptides of the invention are generally described by the formula:

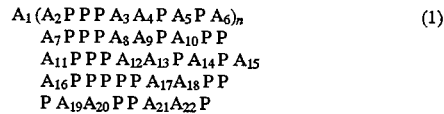

including the N-terminal acylated and/or C-terminal amidated or esterified forms thereof, and the antimicrobial or LPS-binding fragments thereof, where each $A_i$ and n are as defined above. Those peptides of the invention which occur in nature must be in purified and isolated form.

The peptides of Formula (1) or its active fragments may optionally be extended by 1–8, preferably only 1–5 and more preferably only 1–3 noninterfering amino acids at either the N-terminus or C-terminus or both.

The amino terminus of any of the peptides may be in the free amino form or may be acylated by a group of the formula RCO—, wherein R represents a hydrocarbyl group of 1–6C. The hydrocarbyl group is saturated or unsaturated and/or cyclic and is typically, for example, methyl, ethyl, i-propyl, t-butyl, n-pentyl, cyclohexyl, cyclohexen-2-yl, cyclopentyl, hexen-3-yl, hexyn-4-yl, and the like.

The C-terminus of the peptides of the invention may be in the form of the underivatized carboxyl group, either as the free acid or an acceptable salt, such as the potassium, sodium, calcium, magnesium, or other salt of an inorganic ion or of an organic ion such as caffeine. The carboxyl terminus may also be derivatized by formation of an ester with an alcohol of the formula ROH, or may be amidated by an amine of the formula $NH_3$, or $RNH_2$, or $R_2NH$, wherein each R is independently hydrocarbyl of 1–6C as defined above. Carboxy termini of the formula —COOH and its salts or —$CONH_2$ are preferred. Amidated forms of the peptides wherein the C-terminus has the formula —$CONH_2$ are especially preferred.

As the prophenin peptides of the invention contain basic amino acids, the peptides of the invention may be supplied in the form of the acid addition salts. Typical acid addition salts include those of inorganic ions such as chloride, bromide, iodide, fluoride or the like, sulfate, nitrate, or phosphate, or may be salts of organic anions such as acetate, formate, benzoate and the like. The acceptability of each of such salts is dependent on the intended use, as is commonly understood. If the peptides of the invention are prepared under physiological conditions, the side-chain amino groups of basic amino acids will be in the form of the relevant acid addition salts.

The peptides of the invention may contain 1–2 amino acid residues in the D, rather than in the native L form.

The amino acid notations used herein are conventional and are as follows:

| Amino Acid | One-Letter Symbol | Three-letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The amino acid homoargenine, not encoded genetically, is abbreviated Har.

In the specific peptides shown in the present application, the L-form of any amino acid residue having an optical isomer is intended unless the D-form is expressly indicated by a dagger superscript (†).

In all of the peptides of the invention, one or more amide linkages (—CO—NH—) may optionally be replaced with another linkage which is an isostere such as —$CH_2NH$—, —$CH_2S$—, —$CH_2CH_2$, —CH=CH— (cis and trans), —$COCH_2$, —$CH(OH)CH_2$— and —$CH_2SO$—. This replacement can be made by methods known in the art. The following references describe preparation of peptide analogs which include these alternative-linking moieties: Spatola, A. F., *Vega Data* (Mar. 1983), Vol. 1, Issue 3, "Peptide Backbone Modifications" (general review); Spatola, A. F., in "Chemistry and Biochemistry of Amino Acids Peptides and Proteins," B. Weinstein, eds., Marcel Dekker, New York. p. 267 (1983) (general review); Morley, J. S., *Trends. Pharm Sci* (1980) pp. 463–468 (general review); Hudson, D., et al., *Int J Pept Prot Res* (1979) 14:177–185 (—$CH_2NH$—, —$CH_2CH_2$—); Spatola, A. F., et al., *Life Sci* (1986) 38:1243 1249 (—$CH_2$—S); Hann, M. M., *J Chem Soc Perkin Trans I* (1982) 307–314 (—CH—CH—, cis and trans); Almquist, R. G., et al., *J Med Chem* (1980) 23:1392–1398 (—$COCH_2$—); Jennings-White, C., et al., *Tetrahedron Lett* (1982) 23:2533 (—$COCH_2$—); Szelke, M., et al., European Application EP 45665 (1982) CA:97:39405 (1982) (—CH(OH)$CH_2$—); Holladay, M. W., et al., *Tetrahedron Lett* (1983) 24:4401–4404 (—C(OH) $CH_2$—); and Hruby, V. J., *Life Sci* (1982) 31:189–199 (—$CH_2$—S—).

In an alternative embodiment, the peptides of the invention are defined as described by Formula (1) but wherein the specific peptide in each case is determined by the isolatability of the peptide from mammalian leukocytes, preferably porcine leukocytes, by the invention method. The invention method comprises the steps of providing an ultrafiltrate of a lysate of porcine leukocytes and isolating antimicrobial peptides of about 79 amino acids. These peptides can further be defined by the ability of DNA encoding them to hybridize under stringent conditions to the DNA from porcine leukocytes encoding the peptide exemplified as Proph1 herein.

Preferred Embodiments

In general, peptides of Formula (1) wherein each of $A_2$, $A_4$, $A_7$, $A_9$, $A_{11}$, $A_{13}$, $A_{16}$, $A_{17}$, $A_{19}$ and $A_{22}$ is independently selected from the group consisting of Val, Ile and Phe are preferred. Also preferred are those wherein each of $A_5$, $A_{10}$, $A_{14}$ and $A_{20}$ is Gly and $A_1$ is Ala or wherein each of $A_6$, $A_{18}$ and $A_{21}$ is Arg or wherein $A_{15}$ is Trp or wherein n is 4. Especially preferred are those embodiments wherein $A_{12}$ is Val or Ile and $A_2$, $A_7$, $A_9$, $A_{11}$, $A_{13}$, $A_{16}$, $A_{17}$, and $A_{19}$ are Phe or Val and especially wherein $A_2$, $A_7$, $A_{11}$ and $A_{16}$ are Phe.

Particularly preferred compounds of the invention are selected from the group consisting of

```
A F P P P N V P G P R
  F P P P N F P G P R
  F P P P N F P G P R
  F P P P N F P G P R
  F P P P N F P G P P
  F P P P I F P G P W
  F P P P P P F R P P
  P F G P P R F P;

A F P P P N V P G P R
  F P P P N F P G P R
  F P P P N I P G P R
  F P P P N F P G P R
  F P P P N F P G P P
  F P P P I F P G P W
  F P P P P P F R P P
  P F G P P R F P;

A F P P P N V P G P R
  F P P P N F P G P R
  F P P P N F P G P R
  F P P P N F P G P R
  F P P P N F P G P P
  F P P P I F P G P R
  F P P P P P F R P P
  P F G P P R F P;
```

```
                        -continued
              A  F  P  P  P  N  V  P  G  P  R
                 F  P  P  P  N  F  P  G  P  R
                 F  P  P  P  N  F  P  G  P  R
                 F  P  P  P  N  F  P  G  P  Har
                 F  P  P  P  N  F  P  G  P  P
                 F  P  P  P  I  F  P  G  P  W
                 F  P  P  P  P  P  F  R  P  P
                 P  F  G  P  P  K  F  P;

A  F  P  P  P  N  V  P  G  P  R
                 F  P  P  P  Q  F  P  G  P  R
                 F  P  P  P  N  F  P  G  P  R
                 F  P  P  P  Q  F  P  G  P  R
                 F  P  P  P  N† F  P  G  P  P
                 F  P  P  P  V  F  P  G  P  W
                 F  P  P  P  P  P  F  R  P  P
                 P  F  G  P  P  R  F  P;

A  F  P  P  P  N  V  P  G  P  K
                 F  P  P  P  N  I  P  G  P  R
                 F  P  P  P  N  I  P  G  P  R
                 F  P  P  P  N  F  P  G  P  R
                 F  P  P  P  N  F  P  G  P  P
                 F  P  P  P  I  F  P  G  P  W
                 F  P  P  P  P  P  F  Har P  P
                 P  F  G  P  P  R  F  P;

A  F  P  P  P  N  V  P  G  P  R
                 V  P  P  P  N  F  P  G  P  R
                 F  P  P  P  N  F  P  G  P  R†
                 F  P  P  P  N  F  P  G  P  R
                 I  P  P  P  N  F  P  G  P  P
                 F  P  P  P  I  F  P  G  P  W
                 F  P  P  P  P  P  F  R  P  P
                 P  F  G  P  P  R  F  P;  and A  F  P  P  P  N  F  P  G  P  R
                 F  P  P  P  N  F  P  G  P  R
                 V  P  P  P  N  F  P  G  P  R
                 F  P  P  P  N  F  P  G  P  R
                 F  P  P  P  N  F  P  G  P  P
                 F  P  P  P  I  F  P  G  P  W
                 F  P  P  P  P  P  F  R  P  P
                 P  F  G  P  P  R  F  P,
``` wherein the C-terminal carboxy is —COOH or its salts or is —CONH$_2$, especially Prophl.

Active fragments of the invention include those of the formula selected from the group consisting of:

$$A_1A_2 \; P \; P \; P \; A_3 \; A_4 \; P \; A_5 \; P \; A_6; \quad (1a)$$

$$A_7 \; P \; P \; P \; A_8 \; A_9 \; P \; A_{10} \; P \; P; \quad (1b)$$

$$A_{11} \; P \; P \; P \; A_{12}A_{13} \; P \; A_{14} \; P \; A_{15}; \quad (1c)$$

$$A_{16} \; P \; P \; P \; P \; P \; P \; A_{17}A_{18} \; P \; P; \quad (1d)$$

and $$P \; A_{19}A_{20} \; P \; P \; A_{21}A_{22} \; P; \quad (1e)$$

and the composites thereof. Thus, each of the above fragments may be used per se or may be ligated to an identical fragment or to a different fragment up to a total of 79 amino acids.

Preparation of the Invention Compounds

Standard methods of synthesis of peptides are known. Most commonly used currently are solid phase synthesis techniques; indeed, automated equipment for systematically constructing peptide chains can be purchased. Solution phase synthesis can also be used but is considerably less convenient. When synthesized using these standard techniques, amino acids not encoded by gene, and/or D-enantiomers can be employed in the synthesis. Thus, one very practical way to obtain the compounds of the invention is to employ these standard chemical synthesis techniques.

In addition to providing the peptide backbone, the N- and/or C-terminus can be derivatized, again using conventional chemical techniques. The compounds of the invention may optionally contain an acyl group, preferably an acetyl group at the amino terminus. Methods for acetylating or, more generally, acylating, the free amino group at the N-terminus are generally known in the art; in addition, the N-terminal amino acid may be supplied in the synthesis in acylated form.

At the carboxy terminus, the carboxyl group may of course, be present in the form of a salt; in the case of pharmaceutical compositions this will be a pharmaceutically acceptable salt. Suitable salts include those formed with inorganic ions such as $NH_4^+$, $Na^+$, $K^+$, $Mg^{++}$, $Ca^{++}$, and the like as well as salts formed with organic cations such as those of caffeine and other highly substituted amines. The carboxy terminus may also be esterified using alcohols of the formula ROH wherein R is hydrocarbyl (1–6C) as defined above. Similarly, the carboxy terminus may be amidated so as to have the formula —CONH$_2$, —CONHR, or —CONR$_2$, wherein each R is independently hydrocarbyl (1–6C) as herein defined. Techniques for esterification and amidation as well as neutralizing in the presence of base to form salts are all standard organic chemical techniques.

If the peptide backbone is comprised entirely of gene-encoded amino acids, or if some portion of it is so composed, the peptide or the relevant portion may also be synthesized using recombinant DNA techniques. A nucleic acid molecule encoding the peptides of the invention may itself be synthesized using commercially available equipment; codon choice can be integrated into the synthesis depending on the nature of the host. Alternatively, although less convenient, an encoding DNA can be obtained, at least initially, by screening a cDNA library prepared from porcine leukocytes using probes or PCR primers based on the amino acid sequences of the prophenins described herein. This results in recovery of the naturally occurring sequence encoding the prophenins of the invention. Obtention of this native sequence is significant for purposes other than the synthesis of the prophenins per se; the availability of the naturally occurring sequences provides a useful probe or permits the design of an appropriate amplification primer to obtain corresponding active DNA encoding prophenins of other species. Thus, cDNA libraries, for example, of leukocytes derived from other animals can be amplified using these primers or screened using the native DNA, preferably under conditions of high stringency. High stringency is as defined by Maniatis, et al. *Molecular Cloning: a Laboratory Manual* 2nd Ed, Cold Spring Harbor Laboratory Press (1989), the relevant portions of which are incorporated herein by reference. These procedures also permit recovery of allelic variants of these peptides from the same species.

Alternatively, the prophenins can be prepared by isolation from leukocytes of an animal species using techniques similar to those disclosed herein for the isolation of porcine prophenins. In general, these techniques involve preparing a lysate of a leukocyte preparation, ultrafiltering the supernatant of the clarified lysate and recovering the ultrafiltrate. The ultrafiltrate is then subjected to chromatographic separation. The location of fragments having antimicrobial activity corresponding to prophenins can be assessed using criteria of molecular weight and assaying the fractions for the desired activities as described herein.

Isolated and recombinantly produced forms of the prophenins may require subsequent derivatization to modify the N- and/or C-terminus. Depending on the host organism used for recombinant production and the animal source from which the protein is isolated, some or all of these conversions may already have been effected.

For recombinant production, the nucleotide sequence encoding the prophenins of the invention is included in an expression system which places these coding sequences under control of a suitable promoter and other control sequences compatible with an intended host cell. Types of host cells available span almost the entire range of the plant and animal kingdoms. Thus, the prophenins of the invention could be produced in bacteria or yeast (to the extent that they can be produced in a nontoxic or refractile form or utilize resistant strains) as well as in animal cells, insect cells and plant cells. Indeed, modified plant cells can be used to regenerate plants containing the relevant expression systems so that the resulting transgenic plant is capable of self protection vis-à-vis these infective agents. In principle, transgenic nonhuman animals containing these expression systems could also be obtained. In this embodiment, generally, viral control sequences are useful.

The prophenins of the invention can be produced recombinantly in a form that will result in their secretion from the host cell by fusing to the nucleotide sequence encoding the prophenin, a nucleotide sequence encoding a suitable signal peptide. The prophenin may also be produced intracellularly. Prophenins may also be produced as fusion proteins with additional amino acid sequence which may or may not need to be subsequently removed prior to the use of these compounds as antimicrobials.

Thus, the prophenins of the invention can be produced in a variety of modalities including chemical synthesis, recombinant production, isolation from natural sources, or some combination of these techniques.

In particular, the active fragments of the prophenins can be prepared and used as fragments per se, or can be ligated together as composites. For example, fragment (1a) may be ligated to one or two additional (1a) fragments, or to (1b) or to (1c) or to (1e) or to multiples thereof.

Those members of the prophenin class which occur naturally are supplied in purified and isolated form. By "purified and isolated" is meant free from the environment in which the peptide normally occurs (in the case of such naturally occurring peptides) and in a form where it can be used practically. Thus, "purified and isolated" form means that the peptide is substantially pure, i.e., more than 90% pure, preferably more than 95% pure and more preferably more than 99% pure or is in a completely different context such as that of a pharmaceutical preparation.

Antibodies

Antibodies to the prophenins of the invention may also be produced using standard immunological techniques for production of polyclonal antisera and, if desired, immortalizing the antibody-producing cells of the immunized host for sources of monoclonal antibody production. Techniques for producing antibodies to any substance of interest are well known. It may be necessary to enhance the immunogenicity of the substance, particularly as here, where the material is only a short peptide, by coupling the hapten to a carrier. Suitable carriers for this purpose include substances which do not themselves produce an immune response in the mammal to be administered the hapten-carrier conjugate. Common carriers used include keyhole limpet hemocyanin (KLH), diphtheria toxoid, serum albumin, and the viral coat protein of rotavirus, VP6. Coupling of the hapten to the carrier is effected by standard techniques such as contacting the carrier with the peptide in the presence of a dehydrating agent such as dicyclohexylcarbodiimide or through the use of linkers such as those available through Pierce Chemical Company, Chicago, Ill.

The prophenins of the invention in immunogenic form are then injected into a suitable mammalian host and antibody titers in the serum are monitored. Polyclonal antisera may be harvested when titers are sufficiently high. Alternatively, antibody-producing cells of the host such as spleen cells or peripheral blood lymphocytes may be harvested and immortalized. The immortalized cells are then cloned as individual colonies and screened for the production of the desired monoclonal antibodies.

The antibodies of the invention are, of course, useful in immunoassays for determining the amount or presence of the prophenins. Such assays are essential to quality controlled production of compositions containing the prophenins of the invention. In addition, the antibodies can be used to assess the efficacy of recombinant production of the prophenins, as well as screening expression libraries for the presence of prophenin encoding genes.

Compositions Containing the Prophenins and Methods of Use

The prophenins of the invention are effective in inactivating a wide range of microbial targets, including Gram-positive and Gram-negative bacteria and yeast but are particularly highly specific for Gram-negative bacteria. Accordingly, they can be used in disinfectant compositions and as preservatives for materials such as foodstuffs, cosmetics, medicaments, or other materials containing nutrients for organisms. For use in such contexts, the prophenins (or fragments or composites) are supplied either as a single prophenin (or fragment or composite), in admixture with several other prophenins (or fragments or composites), or in admixture with additional antimicrobial agents. In general, as these are preservatives in this context, they are usually present in relatively low amounts, of less than 5%, by weight of the total composition, more preferably less than 1%, still more preferably less than 0.1%.

The peptides of the invention are also useful as positive controls in antimicrobial assays, especially for assays against Gram-negative bacteria.

For use as antimicrobials in the treatment of animal subjects, the prophenins and/or fragments and/or composites can be formulated as pharmaceutical or veterinary compositions. Depending on the subject to be treated, the mode of administration, and the type of treatment desired—e.g., prevention, prophylaxis, therapy; the prophenins and related peptides are formulated in ways consonant with these parameters. A summary of such techniques is found in Remington's *Pharmaceutical Sciences*, latest edition, Mack Publishing Co., Easton, Pa.

The prophenins and/or fragments and/or composites can be administered singly or as mixtures of several prophenins, and/or fragments and/or composites, or in combination with other pharmaceutically active components. The formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. The formulation will generally include a diluent as well as, in some cases, adjuvants, buffers, preservatives and the like. The peptides of the invention can be administered also in liposomal compositions or as microemulsions.

If administration is to be oral, the peptides of the invention must be protected from degradation in the stomach using a suitable enteric coating. This may be avoided to some extent by utilizing amino acids in the D-configuration, thus providing resistance to proteases. However, the peptide is still susceptible to hydrolysis due to the acidic conditions of the stomach; thus, some degree of enteric coating may still be required.

The peptides of the invention may also be applied to plants or to their environment to prevent microbial-induced diseases in these plants. Suitable compositions for this use will typically contain a diluent as well as a spreading agent or other ancillary agreements beneficial to the plant or to the environment.

Thus, the peptides of the invention may be used in any context wherein an antimicrobial action is required. This use may be an entirely in vitro use, or the peptides may be administered to organisms.

In addition, the antimicrobial activity may be generated in situ by administering an expression system suitable for the production of the peptides of the invention. Such expression systems can be supplied to plant and animal subjects using known techniques. For example, in animals, pox-based expression vectors can be used to generate the peptides in situ. Similarly, plant cells can be transformed with expression vectors and then regenerated into whole plants which are capable of their own production of the peptides.

As shown hereinbelow, the prophenins and their fragments are capable of inactivating endotoxins derived from Gram-negative bacteria—i.e., the lipopolysaccharides (LPS) —in standard assays. Accordingly, the peptides of the invention may be used under any circumstances where inactivation of LPS is desired. One such situation is as a positive control in tests for LPS binding, analogous to the manner in which polymyxin-B is used in Example 3 hereinbelow. Another such situation is in the treatment or amelioration of Gram-negative sepsis.

The following examples are intended to illustrate but not to limit the invention.

EXAMPLE 1

Purification of Prophenin

Fresh porcine blood was collected at an abattoir into 15 liter vessels that contained an anticoagulant, 5% EDTA in normal saline, pH 7.4 (33 ml/L blood). After the blood cells had sedimented spontaneously for 90 min at room temperature, the leukocyte-rich supernatant was removed and centrifuged at 200×g for 5–7 min. The sediments were pooled and suspended in 0.84% ammonium chloride to lyse the erythrocytes. The resulting leukocytes (70–75% PMN, 5–10% eosinophils, 15–25% lymphocytes and monocytes) were washed in normal saline, resuspended in ice cold 10% acetic acid at $10^8$ cells/ml, homogenized and stirred overnight at 4° C. This preparation was centrifuged at 25,000×g for 3 h at 4° C. and its supernatant was lyophilized and weighed.

Lyophilized extract (950 mg dry weight) contained 520 mg of protein by BCA analysis. It was stirred overnight at 4° C. in 100 ml of 10% acetic acid, and then centrifuged at 25,000×g for 2 h. the supernatant was removed and passed by pressure through a 50 ml stirred ultrafiltration cell (Amicon, Danvers, Mass.) that contained YM-5 filter. The ultrafiltrate (24.5 mg of protein by BCA) was concentrated to 3 ml by vacuum centrifugation (Speed Vac Concentrator, Savant Instruments, Hicksville, N.Y.), applied to a 2.5×117 cm column of BioGel P-10 (BioRad, Hercules, Calif.), eluted at 4° C. with 5% acetic acid, and collected in 6.6 ml fractions.

Aliquots (66 μl) of each fraction were dried by vacuum centrifugation, and resuspended in approximately 6.6 μl of 0.01% acetic acid. Five μl samples of this concentrate were tested for antimicrobial activity against *E. coli* ML-35, *L. monocytogenes*, Strain EGD and *C. albicans*, strain 820 by radial diffusion and gel overlay techniques (Lehrer, R. I. et al. *J Immunol Meth* (1991) 137:167–173). Active fractions were further examined by acid-urea PAGE and SDS-PAGE. Prophenins emerged from the P10 column in fractions 38–43 (39.6 ml total volume), which contained a total of 18 mg protein BCA analysis. The elution curve is shown in FIG. 1.

Figure 2:
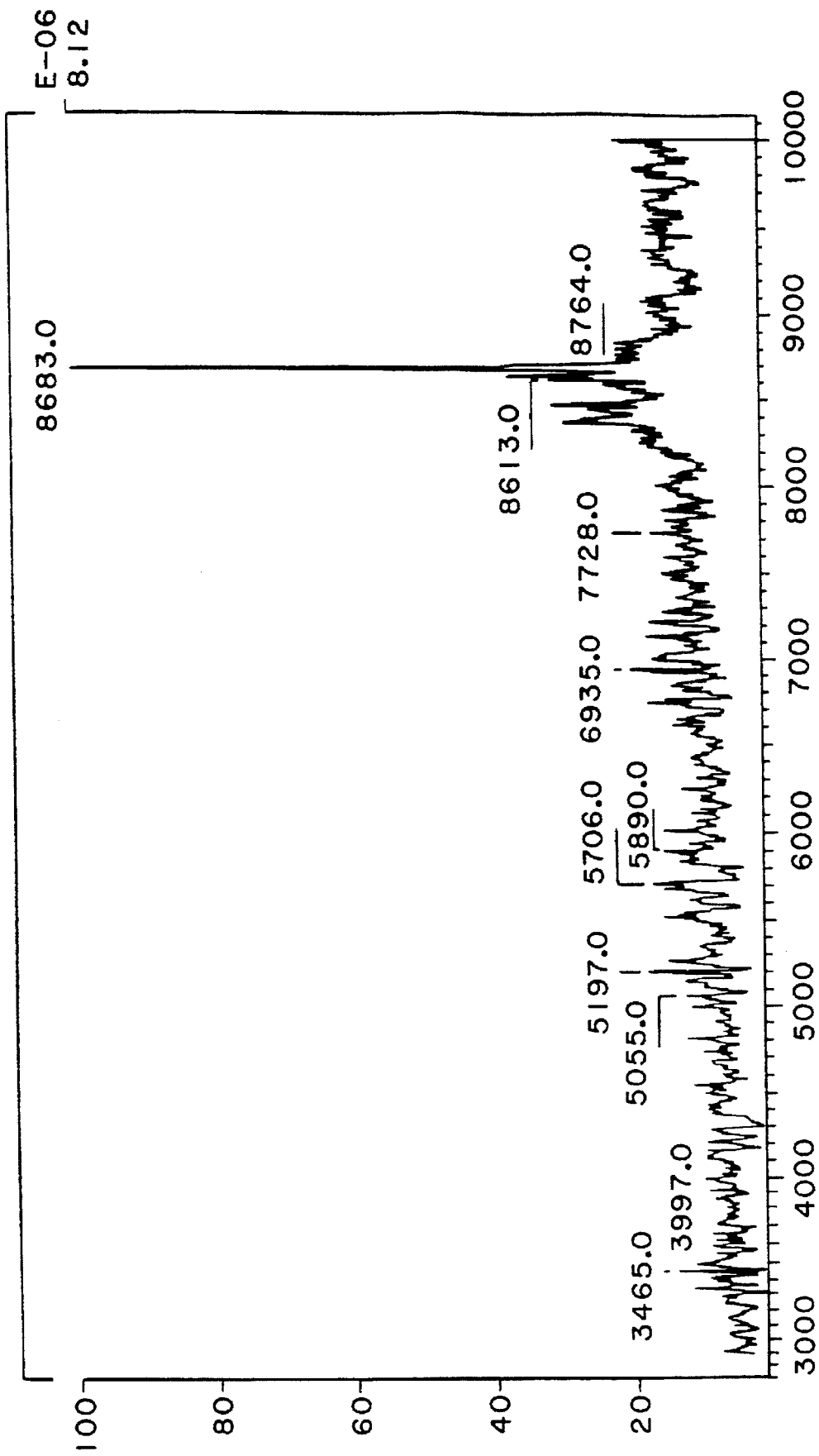
FIG. 2 shows the results of mass spectral determination of Proph1.

The prophenins eluted late (≈48% acetonitrile from a C-18 RP-HPLC column, well after the majority of other leukocyte-derived peptides had emerged. SDS-PAGE indicated a size of 6–7 kDa and AU-PAGE showed the presence of at least two distinct molecular species whose overall amino acid composition was approximately 44% proline, 14% phenylalanine and 8% arginine. After final purification, approximately 400 μg of prophenin-1 and 1 mg of "prophenin-2" were recovered. Prophenin-1, the more cationic form, was purified by preparative CAU-PAGE, followed by RP-HPLC, and appeared homogeneous on AU-PAGE and SDS-PAGE and was virtually homogeneous on electrospray-mass spectroscopy. The mass of Prophenin: was 8,683 by ESI-MS, consistent with its calculated mass (8685) from the sequence shown herein. The minor peak (mass 8613) represented des $Ala_1$-prophenin-1. These data are shown in FIG. 2.

Although Prophenin-2 appeared homogeneous by AU-PAGE, SDS-PAGE and RP-HPLC, ESI-MS analysis revealed the presence of two species, with masses of 8,807 and 8,794. "Prophenin-2" is thus a mixture of two closely related prophenins that differ in primary sequence from each other and from prophenin-1. The amino acid analysis of the "Prophenin-2" mixture showed that none of Cys, Ser, His, Tyr, Met, Leu and Lys were present; Trp was not determined.

| Amino acid analysis of "Prophenin-2" | | | | |
|---|---|---|---|---|
| Residue | pmols detected | mols % detected | Residues per 78 res. | Comments relative to PF-1 |
| Asx | 1.365 | 6.78 | 5.3 | |
| Glx | 0.356 | 1.77 | 1.4 | more |
| Gly | 2.312 | 11.48 | 9.0 | |
| Arg | 2.104 | 10.45 | 8.2 | more |
| Ala | 0.265 | 1.32 | 1.0 | |
| Pro | 9.784 | 48.6 | 37.9 | less |
| Val | 0.310 | 1.54 | 1.2 | |
| Ile | 0.200 | 0.99 | 0.8 | |
| Phe | 3.433 | 17.1 | 13.3 | more |

Amino acid sequences were determined by gas-phase Edman degradation with a Porton Model 2090 instrument, using purified a 1 nmol sample of prophenin-1. The initial yield was 57.6% (576 pmols) and the repetitive yield was 95.98%. The initial sequencing of native prophenin-1 provided unambiguous identification of all but 3 of its initial 65 residues.

To confirm these data and ascertain the remaining residues, a tryptic digest was prepared by incubating 17 μg of prophenin-1 in 30 μl of 0.1M ammonium bicarbonate, pH 8.15, with 0.3 μg of TPCK-treated trypsin (Worthington) for up to 3 h at 37° C. The digestion was stopped by adding glacial acetic acid (final conc. 25%), an aliquot was removed for on-line capillary-LC-ESI-MS and the remainder was purified by RP-HPLC on a Vydac C-18 column with a gradient of acetonitrile in 0.1% trifluoroacetic acid. Electrospray ionization (ESI)-mass spectrometric analyses were performed by Kristine Swiderek and Terry D. Lee at the Division of Immunology, Beckman Research Institute of the City of Hope, Duarte, Calif. The sample (approximately 30 pmols) was analyzed as described by Harwig, S. et al. in *Techniques in Protein Chem V* (1994) J. Crabb, ed. Academic Press, N.Y. pp. 81–88.

Figures 3, 4A:
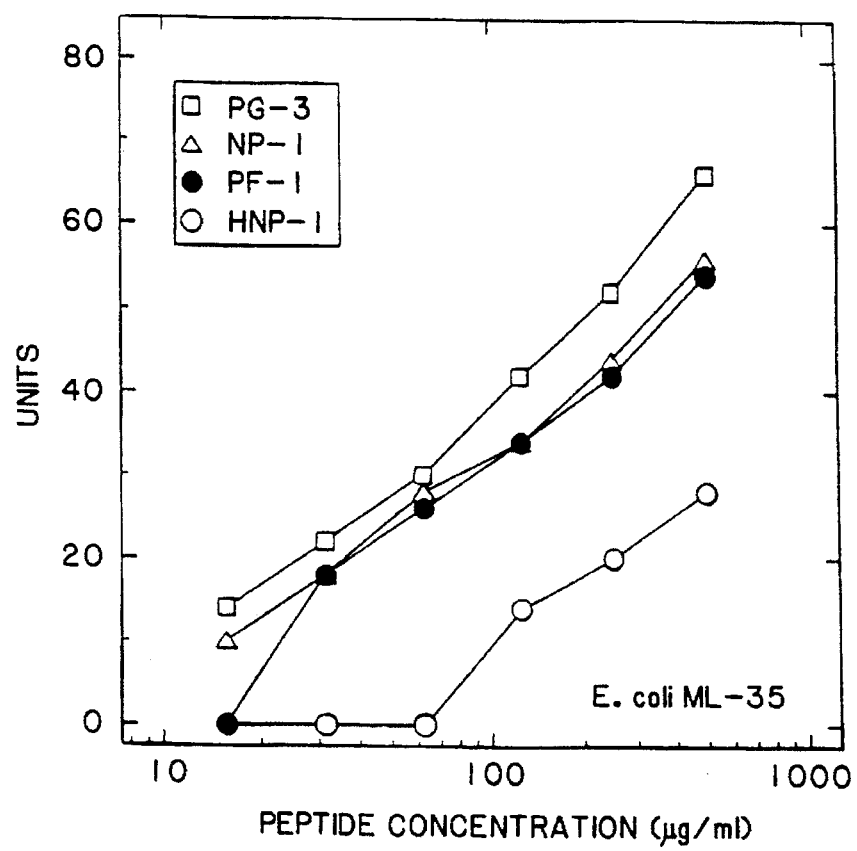
FIG. 3 shows the amino acid sequence of Proph1.
FIG. 4a shows antibacterial activity of Proph1 against *E. Coli*.

The trypsin digest eluted as three broad peaks in Fractions 1, 2 and 3 in the order of their elution from the column. Fraction 1 contained a major component with a mass of 1148, and a minor component with a mass of 1077. It corresponded to an undecamer composed of residues 1–11, with a minor amount of the decamer composed of residues 2–11. Fraction 2 had a mass of 1125 and was about 3× more abundant than Fraction 1. It corresponded to the repeating FPPPNFPGPR decamer found in residues 12–41. Fraction 3 had a mass of 3986. By microsequencing through to residue 76 (proline), we determined that it corresponded to residues 42–77 of prophenin-1. The presence of arginine-77 was confirmed by amino acid analysis and the mass measurement. The amino acid sequence of prophenin-1 is shown in FIG. 3.

EXAMPLE 2

Antimicrobial Activity

The radial diffusion assay in agarose gels as described above was also used to test the activity of the purified prophenins. Samples of 5 µL each were added to 3 mm wells in thin gels composed of 10 mM sodium phosphate, 30 mg/ml trypticase soy broth powder in 1% agarose and containing approximately $4 \times 10^5$ CFU/ml of mid-log phase organisms. After allowing 3 hours for the samples to diffuse into the underlayer gel, a nutrient-rich overlay gel was poured and the plates were incubated for 24 hours at 37° C. to allow surviving organisms to form microcolonies. The diameters of the clear zones were measured and expressed in "units" (10 units=1 mm) as described previously.

Figure 4B:
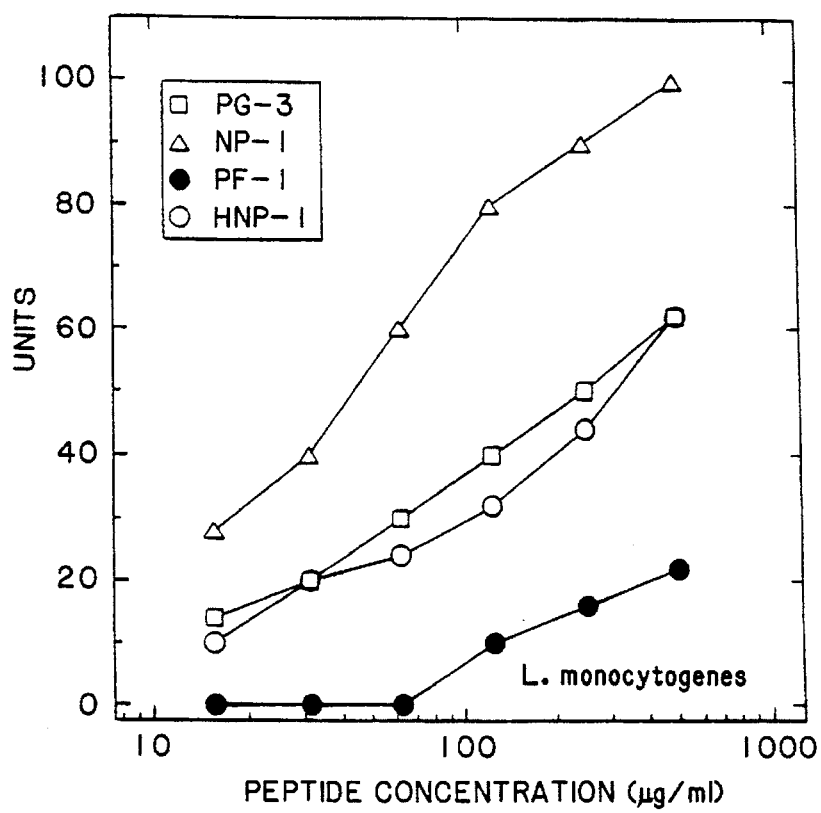
FIG. 4b shows antibacterial activity of Proph1 against *Listeria monocytogenes*.
Figure 4C:
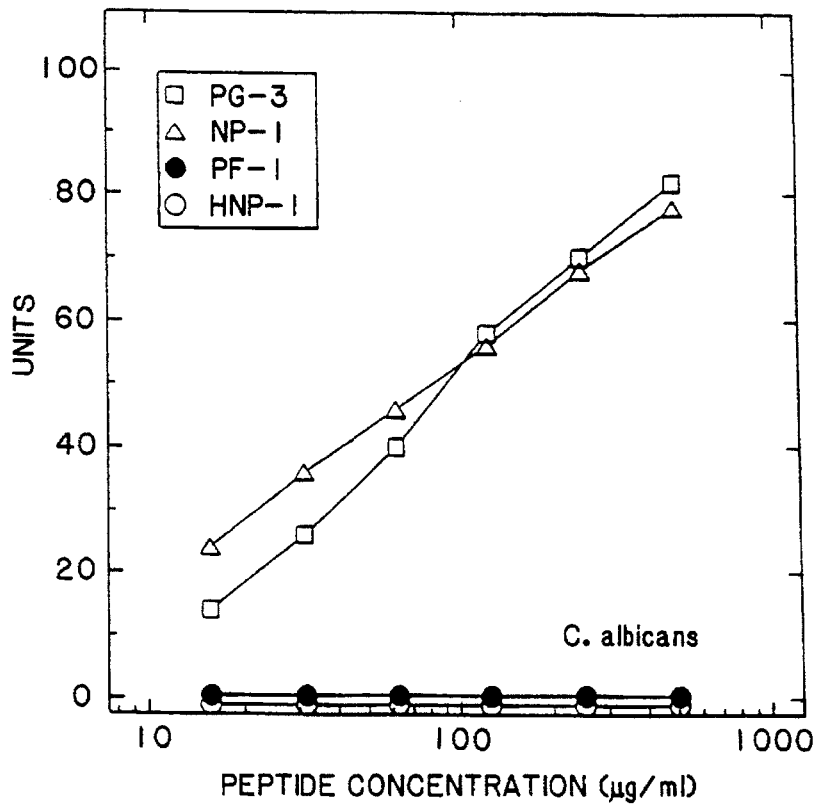
FIG. 4c shows antifungal activity of Proph1 against *Candida albicans*.

FIGS. 4a, 4b and 4c show the results against three test organisms in units described as above. Rabbit defensin (NP-1) and human defensin (HNP-1) and protegrin-3 (PG3) were used as controls.

FIG. 4a shows that prophenin-1 (closed circles) was comparable in inhibitory activity to PG3 and NP1 against *E. coli* ML-35. All of these were more inhibitory than HNP-1.

FIG. 4b shows that prophenin-1 was substantially less inhibitory against *L. monocytogenes* than were the other three antibiotic peptides. However, some activity was shown at concentrations above 100 µg/ml.

FIG. 4c shows that prophenin-1, like HNP-1, is substantially noninhibitory at reasonable concentrations against *C. albicans*. The other two antibiotics tested, PG3 and NP1 were successful antifungals.

Quantitative results are shown in Table 2 which gives the minimal microbicidal concentration for each of the peptides tested in µg/ml.

TABLE 2

| Target | PF-1 | HNP-2 | NP-1 | PG-3 |
|---|---|---|---|---|
| E. coli | 15.2 | 80.0 | 11.5 | 8.6 |
| L. monocytogenes | 122.2 | 12.0 | 3.4 | 9.0 |
| C. albicans | >150 | >150 | 3.7 | 6.9 |

These results show that, unlike the other three peptides tested, prophenin-1 is highly specific for Gram-negative bacteria.

EXAMPLE 3

Ability to Bind Endotoxin

The prophenins of the invention were tested for their ability to bind the lipid polysaccharide (LPS) of the Gram-negative bacterium *E. coli* strain 0.55B5. The assay was the Limulus amebocyte lysate (LAL) test for endotoxins conducted in the presence and absence of the test compounds. The test was conducted using the procedure described in Sigma Technical Bulletin No. 210 as revised in Dec. 1992 and published by Sigma Chemical Company, St. Louis, Mo.

The LAL test is based on the ability of LPS to effect gelation in the commercial reagent E-TOXATE™ which is prepared from the lysate of circulating amebocytes of the Horseshoe Crab *Limulus polyphemus*. As described in the technical bulletin, when exposed to minute quantities of LPS, the lysate increases in opacity as well as viscosity and may gel or clot depending on the concentration of endotoxin. The technical bulletin goes on to speculate that the mechanism appears analogous to the clotting of mammalian blood and involves the steps of activation of a trypsin-like preclotting enzymes by the LPS in the presence of calcium ion, followed by enzymic modifications of a "coagulogen" by proteolysis to produce a clottable protein. These steps are believed tied to the biologically active or "pyrogenic" portion of the molecule. It has been shown previously that detoxified LPS (or endotoxin) gives a negative LAL test.

Polymyxin B is a cyclic 1.2 kD acylated nonapeptide obtained from *Bacillus polymyxa*. Polymyxin B was used as a positive control since it is known to inhibit LPS-induced Limulus hemocyte lysate clotting.

In the assay, the amounts of prophenin-1 and polymyxin B (78% free polymyxin, Sigma) were preincubated in a final volume of 0.2 ml and the test mixtures contained LPS at a final concentration of 0.05 endotoxin unit/ml and E-TOXATE™ at the same concentration. The test compounds were incubated together with the LPS for 15 minutes before the E-TOXATE™ was added to a final volume (after E-TOXATE™ addition) of 0.2 ml. The tubes were then incubated for 60 minutes at 37° C. and examined for the formation of a gel.

In Table 3, ++ signifies a solid gel (no inhibition), + indicates increased viscosity without solid gel formation (partial inhibition) and 0 indicates that gelation was absent (complete inhibition).

TABLE 3

| Peptide (µg/ml) | 10.0 | 5.0 | 2.5 | 1.25 | 0.63 | 0.31 | 0.16 |
|---|---|---|---|---|---|---|---|
| Polymyxin B | 0 | 0 | + | ++ | ++ | ++ | ++ |
| Prophenin-1 | not done | 0 | 0 | 0 | 0 | ++ | ++ |

Complete inhibition was obtained with 5 µg/ml (≈4.2 µM) polymyxin B sulfate and 0.625 µg/ml (≈72 nM) prophenin-1; thus, on a molar basis, Prophenin-1 is approximately 60-fold more potent than polymyxin B sulfate (4.2/0.072) in binding LPS.

The ability of fragments of prophenin-1 to bind LPS was also assayed. Prophenin-1 was digested with TLCK treated trypsin as described above, thus cleaving the protein C-terminal to the initial 4 arginines. The fragments were purified by RP-HPLC, and their identities were verified by ESI-MS and amino acid composition analysis. The three fragments were those obtained as described in Example 1 and are as follows:

Fraction 1: Positions 1–11:
AFPPPNVPGPR

Fraction 2: Positions 12–21, 22–31, or 32–41:

FPPPNFPGPR

Fraction 3: Positions 42–77:

FPPPNFPGPPFPPPIFPGPWFPPPPPFRPPPFGPPR.

The results are shown in Table 4.

TABLE 4

| µg/ml | 10.0 | 5.0 | 2.5 | 1.25 | .625 | .31 | .16 |
|---|---|---|---|---|---|---|---|
| Fraction 1 | 0 | 0 | + | ++ | ++ | ++ | ++ |
| Fraction 2 | 0 | 0 | + | + | ++ | ++ | ++ |
| Fraction 3 | 0 | + | + | + | ++ | ++ | ++ |

Taking into account the molecular masses of the respective Fractions, the data indicate that Fractions 1, 2 and 3 were each effective as between 2–µM, (approximately equivalent polymyxin B on a molar basis) in inhibiting LPS, whereas intact prophenin-1 molecule shows an effective concentration of 35–70 nM. Thus, the subunits of prophenin-1 appear to be useful in binding LPS although the holoprotein is more effective, and indeed more effective than the additive value of the subunits.

We claim:

1. A method to inhibit the growth of a microbe which method comprises contacting a composition which supports the growth of said microbe with a peptide comprising the amino acid sequence AFPPPNVPGPR
FPPPNFPGPR
FPPPNFPGPR
FPPPNFPGPR
FPPPNFPGPP
FPPPIFPGPW
FPPPPPFRPP
PFGPPRFP SEQ ID NO: 1 or antimicrobial fragments thereof comprising at least 10 contiguous amino acid residues in an amount effective to prevent said growth.

2. The method of claim 1 wherein said microbe is capable of growing in a foodstuff.

3. The method of claim 1 wherein said microbe is Gram-negative.

4. A method to inactivate the endotoxin of Gram-negative bacteria, which method comprises contacting said endotoxin with a peptide comprising the amino acid sequence AFPPPNVPGPR
FPPPNFPGPR
FPPPNFPGPR
FPPPNFPGPR
FPPPNFPGPP
FPPPPPFRPP
PFGPPRFP SEQ ID NO: 1 or LPS-binding fragments thereof comprising at least 10 contiguous amino acid residues in an amount effective to inactivate said endotoxin.

5. The method of claim 4 wherein said contacting is in a subject harboring Gram-negative bacteria.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 79 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

```
Ala Phe Pro Pro Pro Asn Val Pro Gly Pro Arg Phe Pro Pro Pro Asn
 1               5                   10                  15

Phe Pro Gly Pro Arg Phe Pro Pro Pro Asn Phe Pro Gly Pro Arg Phe
            20                  25                  30

Pro Pro Pro Asn Phe Pro Gly Pro Arg Phe Pro Pro Pro Asn Phe Pro
            35                  40                  45

Gly Pro Pro Phe Pro Pro Pro Ile Phe Pro Gly Pro Trp Phe Pro Pro
    50                  55                  60

Pro Pro Pro Phe Arg Pro Pro Pro Phe Gly Pro Pro Arg Phe Pro
65                  70                  75
```

( 2 ) INFORMATION FOR SEQ ID NO:2:

( i ) SEQUENCE CHARACTERISTICS:
        ( A ) LENGTH: 79 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

```
Ala Phe Pro Pro Pro Asn Val Pro Gly Pro Arg Phe Pro Pro Pro Asn
 1               5                   10                  15

Phe Pro Gly Pro Arg Phe Pro Pro Pro Asn Ile Pro Gly Pro Arg Phe
            20                  25                  30

Pro Pro Pro Asn Phe Pro Gly Pro Arg Phe Pro Pro Pro Asn Phe Pro
            35                  40                  45

Gly Pro Pro Phe Pro Pro Pro Ile Phe Pro Gly Pro Trp Phe Pro Pro
    50                  55                  60

Pro Pro Pro Phe Arg Pro Pro Pro Phe Gly Pro Pro Arg Phe Pro
65                  70                  75
```

( 2 ) INFORMATION FOR SEQ ID NO:3:

( i ) SEQUENCE CHARACTERISTICS:
        ( A ) LENGTH: 79 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

```
Ala  Phe  Pro  Pro  Pro  Asn  Val  Pro  Gly  Pro  Arg  Phe  Pro  Pro  Asn
 1                    5                        10                       15

Phe  Pro  Gly  Pro  Arg  Phe  Pro  Pro  Pro  Asn  Phe  Pro  Gly  Pro  Arg  Phe
              20                        25                        30

Pro  Pro  Pro  Asn  Phe  Pro  Gly  Pro  Arg  Phe  Pro  Pro  Pro  Asn  Phe  Pro
          35                        40                        45

Gly  Pro  Pro  Phe  Pro  Pro  Pro  Ile  Phe  Pro  Gly  Pro  Arg  Phe  Pro  Pro
     50                        55                        60

Pro  Pro  Pro  Phe  Arg  Pro  Pro  Pro  Phe  Gly  Pro  Pro  Arg  Phe  Pro
 65                       70                        75
```

( 2 ) INFORMATION FOR SEQ ID NO:4:

( i ) SEQUENCE CHARACTERISTICS:
        ( A ) LENGTH: 79 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 41
        ( D ) OTHER INFORMATION: /note="This position is Har."

( x i ) SEQUENCE DESCRIPTION: SEQ ID NO:4:

```
Ala  Phe  Pro  Pro  Pro  Asn  Val  Pro  Gly  Pro  Arg  Phe  Pro  Pro  Asn
 1                    5                        10                       15

Phe  Pro  Gly  Pro  Arg  Phe  Pro  Pro  Pro  Asn  Phe  Pro  Gly  Pro  Arg  Phe
              20                        25                        30

Pro  Pro  Pro  Asn  Phe  Pro  Gly  Pro  Asn  Phe  Pro  Pro  Pro  Asn  Phe  Pro
          35                        40                        45

Gly  Pro  Pro  Phe  Pro  Pro  Pro  Ile  Phe  Pro  Gly  Pro  Trp  Phe  Pro  Pro
     50                        55                        60

Pro  Pro  Pro  Phe  Arg  Pro  Pro  Pro  Phe  Gly  Pro  Pro  Lys  Phe  Pro
 65                       70                        75
```

( 2 ) INFORMATION FOR SEQ ID NO:5:

( i ) SEQUENCE CHARACTERISTICS:
        ( A ) LENGTH: 78 amino acids
        ( B ) TYPE: amino acid
        ( C ) STRANDEDNESS: single
        ( D ) TOPOLOGY: linear ( x i ) SEQUENCE DESCRIPTION: SEQ ID NO:5:

```
Ala  Phe  Pro  Pro  Pro  Asn  Val  Pro  Gly  Pro  Arg  Phe  Pro  Pro  Gln
 1                    5                        10                       15

Phe  Pro  Gly  Pro  Arg  Phe  Pro  Pro  Pro  Asn  Phe  Pro  Gly  Pro  Arg  Phe
              20                        25                        30

Pro  Pro  Pro  Gln  Phe  Pro  Gly  Pro  Arg  Phe  Pro  Pro  Pro  Phe  Pro  Gly
          35                        40                        45

Pro  Pro  Phe  Pro  Pro  Pro  Val  Phe  Pro  Gly  Pro  Trp  Phe  Pro  Pro  Pro
     50                        55                        60
```

```
Pro  Pro  Phe  Arg  Pro  Pro  Pro  Phe  Gly  Pro  Pro  Arg  Phe  Pro
 65             70                       75
```

(2) INFORMATION FOR SEQ ID NO:6:

(i) SEQUENCE CHARACTERISTICS:
        (A) LENGTH: 79 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 69
        (D) OTHER INFORMATION: /note="This position is Har."

(xi) SEQUENCE DESCRIPTION: SEQ ID NO:6:

```
Ala  Phe  Pro  Pro  Pro  Asn  Val  Pro  Gly  Pro  Lys  Phe  Pro  Pro  Pro  Asn
 1              5                       10                      15

Ile  Pro  Gly  Pro  Arg  Phe  Pro  Pro  Pro  Asn  Ile  Pro  Gly  Pro  Arg  Phe
               20                       25                      30

Pro  Pro  Pro  Asn  Phe  Pro  Gly  Pro  Arg  Phe  Pro  Pro  Pro  Asn  Phe  Pro
               35                       40                      45

Gly  Pro  Pro  Phe  Pro  Pro  Pro  Ile  Phe  Pro  Gly  Pro  Trp  Phe  Pro  Pro
          50                       55                      60

Pro  Pro  Pro  Phe  Asn  Pro  Pro  Pro  Phe  Gly  Pro  Pro  Arg  Phe  Pro
 65                  70                       75
```

(2) INFORMATION FOR SEQ ID NO:7:

(i) SEQUENCE CHARACTERISTICS:
        (A) LENGTH: 78 amino acids
        (B) TYPE: amino acid
        (C) STRANDEDNESS: single
        (D) TOPOLOGY: linear (xi) SEQUENCE DESCRIPTION: SEQ ID NO:7:

```
Ala  Phe  Pro  Pro  Pro  Asn  Val  Pro  Gly  Pro  Arg  Val  Pro  Pro  Pro  Asn
 1              5                       10                      15

Phe  Pro  Gly  Pro  Arg  Phe  Pro  Pro  Pro  Asn  Phe  Pro  Gly  Pro  Phe  Pro
               20                       25                      30

Pro  Pro  Asn  Phe  Pro  Gly  Pro  Arg  Ile  Pro  Pro  Pro  Asn  Phe  Pro  Gly
          35                       40                      45

Pro  Pro  Phe  Pro  Pro  Pro  Ile  Phe  Pro  Gly  Pro  Trp  Phe  Pro  Pro  Pro
          50                       55                      60

Pro  Pro  Phe  Arg  Pro  Pro  Pro  Phe  Gly  Pro  Pro  Arg  Phe  Pro
 65             70                       75
```

(2) INFORMATION FOR SEQ ID NO:8:

(i) SEQUENCE CHARACTERISTICS:
        (A) LENGTH: 79 amino acids
        (B) TYPE: amino acid
        (C) STRANDEDNESS: single
        (D) TOPOLOGY: linear (xi) SEQUENCE DESCRIPTION: SEQ ID NO:8:

```
Ala  Phe  Pro  Pro  Pro  Asn  Phe  Pro  Gly  Pro  Arg  Phe  Pro  Pro  Pro  Asn
 1              5                       10                      15

Phe  Pro  Gly  Pro  Arg  Val  Pro  Pro  Pro  Asn  Phe  Pro  Gly  Pro  Arg  Phe
               20                       25                      30

Pro  Pro  Pro  Asn  Phe  Pro  Gly  Pro  Arg  Phe  Pro  Pro  Pro  Asn  Phe  Pro
               35                       40                      45
```

-continued

```
Gly  Pro  Pro  Phe  Pro  Pro  Pro  Ile  Phe  Pro  Gly  Pro  Trp  Phe  Pro  Pro
     50                       55                      60

Pro  Pro  Pro  Phe  Arg  Pro  Pro  Pro  Phe  Gly  Pro  Pro  Arg  Phe  Pro
65                       70                 75
```

( 2 ) INFORMATION FOR SEQ ID NO:9:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear ( x i ) SEQUENCE DESCRIPTION: SEQ ID NO:9:

```
Phe  Pro  Pro  Pro  Asn  Phe  Pro  Gly  Pro  Pro  Phe  Pro  Pro  Pro  Ile  Phe
1                    5                      10                      15

Pro  Gly  Pro  Trp  Phe  Pro  Pro  Pro  Pro  Pro  Phe  Arg  Pro  Pro  Pro  Phe
              20                       25                           30

Gly  Pro  Pro  Arg
              35
```